United States Patent
Greenberg et al.

[11] Patent Number: 5,810,852
[45] Date of Patent: Sep. 22, 1998

[54] ENDOSCOPIC INTRACORPOREAL SUTURE TYING AID

[75] Inventors: Alex M. Greenberg; Douglas M. Spranger; Paul J. Mulhauser, all of New York, N.Y.; Mark C. Newby, Tuxedo, N.Y.

[73] Assignees: Greenberg Surgical Technologies LLC; Human Factors Industrial Design, Inc., both of New York, N.Y.

[21] Appl. No.: 934,427

[22] Filed: Sep. 19, 1997

Related U.S. Application Data

[63] Continuation of Ser. No. 408,829, Mar. 22, 1995, Pat. No. 5,709,694.

[51] Int. Cl.$^6$ .................................................. A61B 17/00
[52] U.S. Cl. ........................ 606/148; 606/139; 606/147
[58] Field of Search .................................. 606/148, 144, 606/139, 151, 205, 145, 147

[56] References Cited

U.S. PATENT DOCUMENTS

| | | | |
|---|---|---|---|
| 3,955,581 | 5/1976 | Spasiano et al. | 128/334 |
| 4,166,466 | 9/1979 | Jarvik | 128/325 |
| 4,488,523 | 12/1984 | Shichman | 128/334 |
| 5,037,433 | 8/1991 | Wilk et al. . | |
| 5,071,430 | 12/1991 | De Salis et al. | 606/219 |
| 5,074,874 | 12/1991 | Yoon et al. | 606/224 |
| 5,100,421 | 3/1992 | Christoudias | 606/147 |
| 5,147,373 | 9/1992 | Ferzli . | |
| 5,176,691 | 1/1993 | Pierce | 606/148 |
| 5,178,629 | 1/1993 | Kammerer | 606/244 |
| 5,181,919 | 1/1993 | Bergman et al. | 606/144 |
| 5,217,471 | 6/1993 | Burkhart | 606/148 |
| 5,224,948 | 7/1993 | Abe et al. | 606/147 |
| 5,234,444 | 8/1993 | Christoudias | 606/148 |
| 5,234,445 | 8/1993 | Walker et al. | 606/148 |
| 5,234,452 | 8/1993 | Walker et al. . | |
| 5,242,458 | 9/1993 | Bendel et al. | 606/147 |
| 5,250,054 | 10/1993 | Li . | |
| 5,336,231 | 8/1994 | Adair . | |
| 5,423,836 | 6/1995 | Brown . | |
| 5,454,823 | 10/1995 | Richardson et al. . | |
| 5,466,243 | 11/1995 | Schmieding . | |
| 5,499,991 | 3/1996 | Garman et al. . | |
| 5,665,096 | 9/1997 | Yoon | 606/139 |
| 5,741,280 | 4/1998 | Fleenor | 606/148 |

FOREIGN PATENT DOCUMENTS 4127812 of 0000 Germany .

OTHER PUBLICATIONS

Koninckx Suture Grasper and Knotting Device Set, Prof. Koninckx, K.U. Leuven, Storz, Karl Storz—Endoskope, Aug. 1992.

*Primary Examiner*—Michael Powell Buiz
*Assistant Examiner*—Tina T. D. Pham
*Attorney, Agent, or Firm*—Proskauer Rose LLP

[57] ABSTRACT

An endoscopic intracorporeal suture tying aid allows a suture to be looped around itself multiple times and cinched, enabling a throw of a surgeon's knot to be easily made. The tying aid includes a needle holder connected to a proximal end of a shaft for releasably holding a needle; a hook that slides longitudinally with respect to the beaks; and the shaft being axially rotatable with respect to the hook.

18 Claims, 9 Drawing Sheets

ENDOSCOPIC INTRACORPOREAL SUTURE TYING AID

This application is a continuation division of application Ser. No. 08/408,829, filed Mar. 22, 1995, now U.S. Pat. No. 5,709,694.

FIELD OF THE INVENTION

The present invention is directed to a surgical instrument and, more particularly, to an endoscopic suture tying aid.

BACKGROUND OF THE INVENTION

Endoscopic surgery is surgery performed intracorporeally without requiring a large incision. Endoscopic surgery is typically performed by inserting a number of ports through small incisions in the patient's skin to access the surgical site. One of the ports receives an endoscope, which is a video camera-like device. The surgeon views the surgical site via the endoscope and performs the surgery by inserting surgical devices through the ports into the patient. This avoids having to "open up" the patient, resulting in less invasive surgery than conventional procedures.

FIG. 1 illustrates a typical laparoscopic surgery, which is one type of endoscopic surgery. FIG. 1 shows three tubes, or ports 30a, 30b, 30c, inserted through a patient's cutaneous region (skin) 32, through several tissue and muscle layers 34, past the peritoneal membrane 36, which encloses the abdominal cavity, and into the abdominal cavity 38. One port 30a receives a laparoscope 40. The laparoscope 40 is a type of endoscope. The laparoscope 40 provides a light source and may be connected to video equipment for displaying the surgical site on a TV monitor. The port 30a also receives an insufflator 42 which inflates the abdominal cavity with $CO_2$ allowing the organs to be seen, and providing the surgeon with room to manipulate surgical instruments. Laparoscopic surgery is commonly used for many types of abdominal surgery and is also becoming increasingly common in other surgical areas, such as thoracic surgery. This specification describes the invention illustratively with respect to laparoscopic surgery, but a person skilled in the art readily understands that the invention described may be used in many types of endoscopic surgery.

One difficulty facing surgeons performing endoscopic surgery is suturing through the ports 30. A surgeon may wish to tie knots during endoscopic surgery for many reasons. For example, a surgeon may wish to close an incision made in an organ or to tie off a portion of an organ to be removed. One reason suturing is difficult is because of the difficulty in tying knots for sutures located inside the patient, when the surgeon can only access the surgical site through the ports.

This task is difficult for several reasons. The surgeon's approach to the surgical site is limited to the access provided by the available ports. In a typical laparoscopic surgery, for example, the surgical site is typically quite distant from the surgeon's hands. For example, a standard grasping tool used for tying sutures intracorporeally is 14 inches long. Thus, the surgeon's hands are more than a foot away from the surgical site. The surgeon has less control over the surgical instruments than if tying the sutures "hands on", making a simple task much more difficult. Another reason is that the surgeon is not directly viewing the surgical site. Rather, the site is often viewed by watching a video monitor. The surgeon must replace hand-to-eye coordination with hand-to-video coordination. The camera also presents other difficulties, such as difficulties adapting to the depth of field presented, viewing angle, and limited camera frame size.

Intracorporeal suturing and knot tying require several series of movements involving passing the suture and needle from one surgical instrument to another. This series of passes is required for each "bite" of tissue in a simple running stitch.

Even more difficult is knot tying the first and last passes of a run of continuous sutures. A typical knot tied during laparoscopic surgery is a "surgeon's knot". This knot consists of two or three half hitches or "throws" and one reverse half hitch, which is a "locking throw". Intracorporeally, this knot requires multiple passes with grasping the needle and suture. The loops of one throw of the knot are formed by wrapping the needle end of the suture around the shaft of a grasping instrument opposite to the instrument holding the needle. With loops around the grasper's shaft, the suture opposite the instrument holding the needle is picked up. The throw of the knot is then formed by pulling on the suture legs in opposite directions. To complete a surgeon's knot, this must be done three or four times (i.e., three of four throws), depending on the suture thickness. The final knot (the locking throw) must be looped in the direction opposite the other throws. Once the locking throw is complete, the two ends of the suture are secured by a grasper, cut, and removed from the site by withdrawing the grasper from a port.

Several methods are currently used to tie sutures during laparoscopic surgery. One method passes an endoscopically introduced needle through tissue flaps. The needle and suture are withdrawn through a port and a knot is tied outside the patient's body. Using a knot pushing device, the knot is pushed back into the body, securing the tissue flaps. This method has several disadvantages. It requires a long suture length. This suture length makes it difficult to tie continuous sutures. Also, the instruments must be withdrawn from the ports to tie the knots. All of these disadvantages result in a time consuming and inefficient process.

A second method is to use two grasping-type surgical instruments to tie a knot intracorporeally. This method requires greater than usual manual dexterity and replacing hand-to-eye coordination with hand-to-video coordination, because the surgeon must view the surgical site on a monitor screen.

A third method is performed with a device illustrated in FIG. 2. This device is manufactured by Storz, a German company having offices in Culver City, Calif. and sold under the trade name Koninckx. This instrument 50 has a needle grasper 52 and a hood 54 attached to a shaft 56. To tie a knot with the Koninckx device, one end of a suture is grasped with a grasper and the other end is free. Using the Koninckx device, the suture is caught using a hook 55 attached to the hood. The rotating knob 56a is turned 360° to create a loop around the suture leg. Using the grasper, the other end of the suture is now grasped through the loop and pulled through the loop to complete the knot. This knot is not a surgical knot, as preferred by most surgeons performing endoscopic surgery. The Koninckx device cannot tie a true surgeon's knot because the hook cannot rotate around the suture in two directions. Thus, it cannot make the final locking throw in the opposite direction.

It is an object of the present invention to provide an endoscopic device which facilitates tying surgical knots intracorporeally.

SUMMARY OF THE INVENTION

This object is achieved by an endoscopic intracorporeal suture tying aid according to the present invention. The device allows a suture to be looped around itself multiple times and cinched. Preferably, the device allows the suture to be looped in two directions, enabling a surgeon's knot to be easily made.

A preferred structure comprises a needle holder connected to a proximal end of a shaft for releasably holding a needle; a hook which is longitudinally positionable with respect to the needle holder; and a shaft which is axially rotatable with respect to the hook. The hook may be placed in at least two positions; the first position being in the vicinity of the needle holder and the second position being distal to the needle holder.

This device is preferably used as follows. The needle holder holds a needle, which passes a suture through tissue. The hook is then positioned in the vicinity of the needle holder, and the shaft axially is rotated so that the needle rotates, causing the suture to be snared by the hook. The hook is withdrawn, creating a loop and pulling additional suture through the tissue. The shaft is again axially rotated, looping the suture a desired number of times around itself. The hook releases the suture and then the knot is cinched, forming one throw. Multiple "throws" may be formed. A final throw in the opposite direction may be made, thus forming the locking throw of a surgeon's knot.

Another preferred structure includes a longitudinally rotatable hook and a longitudinally extending suture barrel through the shaft. This device is used in a manner similar to the first embodiment, except that when the suture is snared, the hook is rotated longitudinally and distally to withdraw additional suture length through the tissue. The barrel extends to facilitate looping the suture. The barrel is withdrawn into the shaft and the shaft is extended to cinch the suture into a knot. The hook is rotated longitudinally and proximally to release the suture.

Yet another preferred structure has a sheath which rotates with respect to the needle holders.

BRIEF DESCRIPTION OF THE DRAWINGS

This and other features of the invention will become apparent from the following drawings, wherein.

DETAILED DESCRIPTION OF PREFERRED EMBODIMENTS

Figure 3:
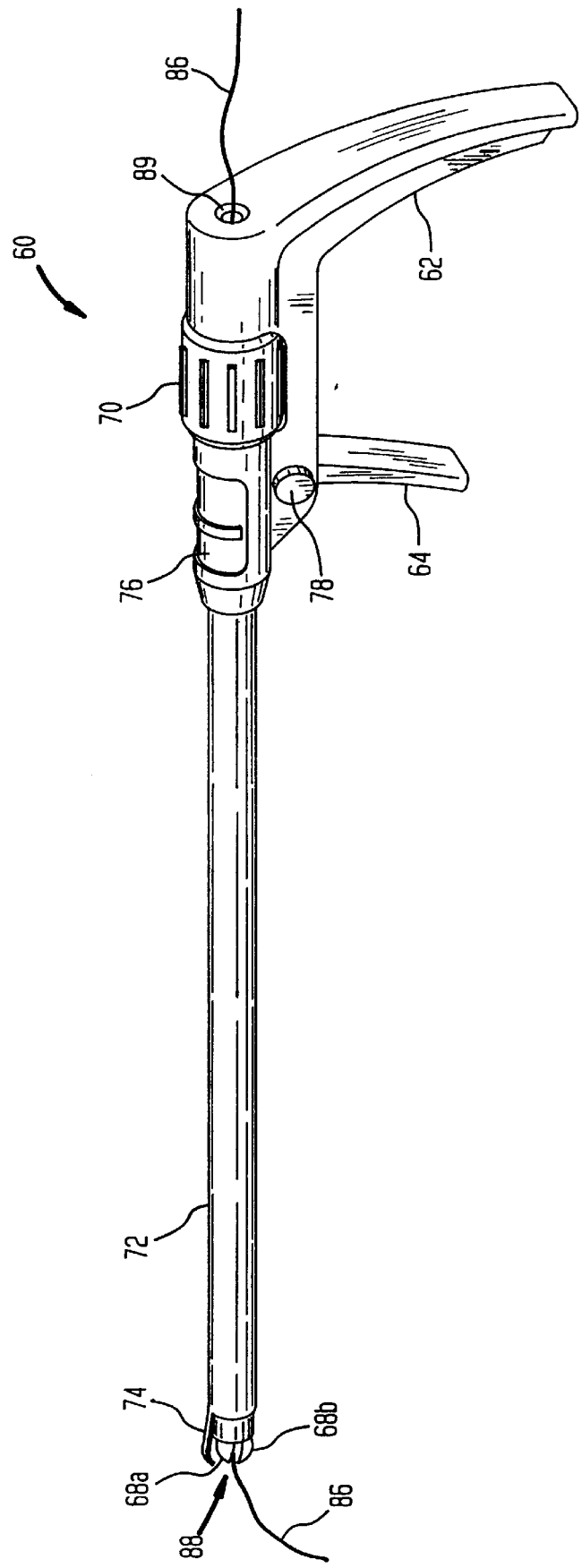
FIG. 3 is a side elevational view of a preferred embodiment of an endoscopic intracorporeal tying aid according to the present invention.
Figure 4A:
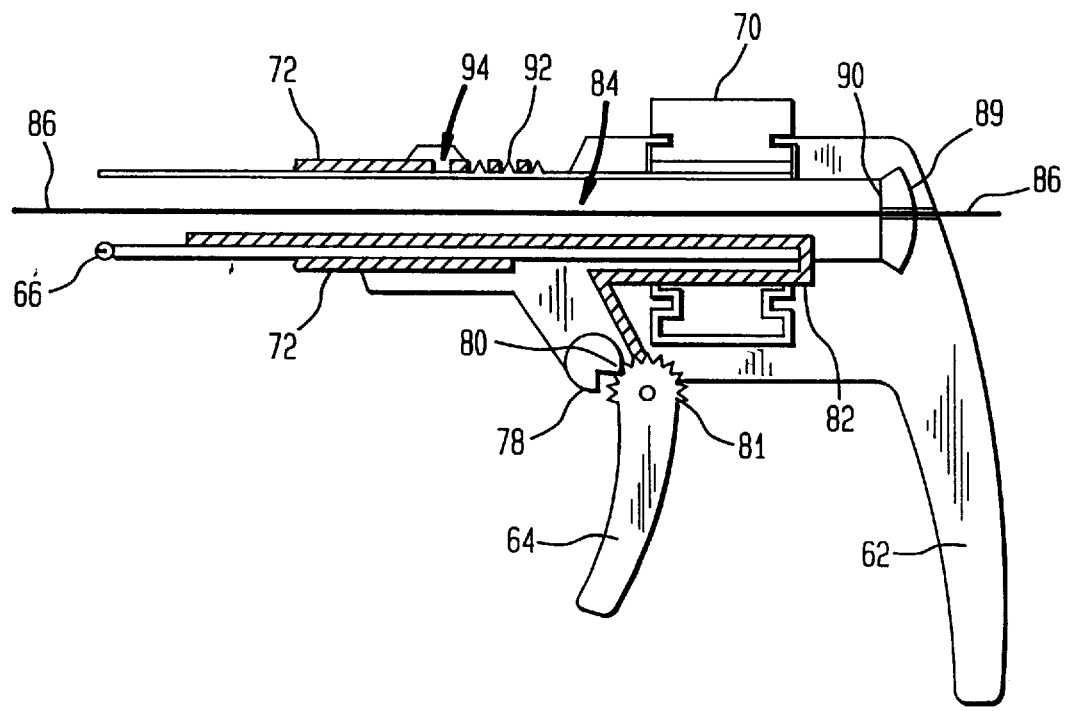
FIGS. 4a and 4b are cutaway views of the device illustrated in FIG. 3.
Figure 4B:
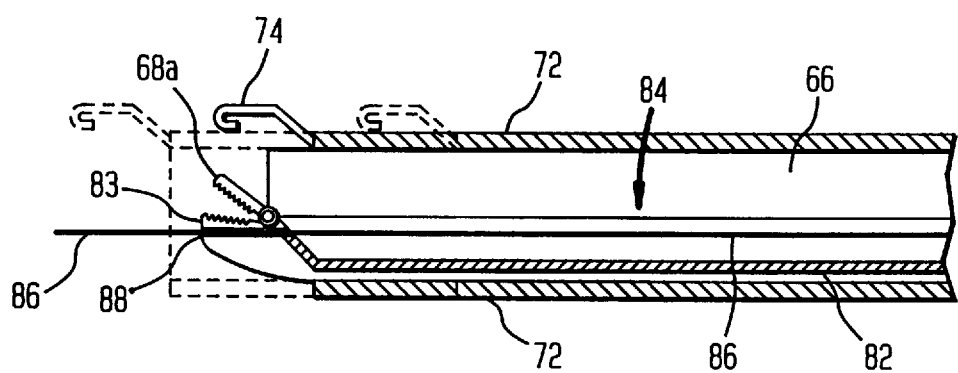

FIGS. 3, 4a, and 4b illustrate a preferred embodiment of an endoscopic intracorporeal suture tying device 60 according to the present invention. The device 60 has a handle 62 and trigger 64. Distal to the trigger is a hollow shaft 66 (see FIGS. 4a, 4b). At the distal end of the hollow shaft 66 is a needle holder 68a, 68b. The shaft may be rotated by turning a knob 70. A positionable sheath 72 runs the exterior length of the hollow shaft 66. At the distal end of the sheath 72 is a hook 74. The hook 74 may be either integrally or fixedly attached to the sheath 72. It is preferable that the hook 74 be flexibly connected to the sheath 72 so that it can fold slightly inward when passed through a port 30. This flexibility is preferably limited to a single plane. That is, it should fold inward but not move side-to-side. The sheath may be retained in several different positions by a sheath positioner 76.

The handle 62, trigger 64, and sheath positioner 76 may be made of any material commonly used for surgical devices such as plastic, stainless steel, or other suitable material. The shaft 66 is preferably made of a suitable biocompatible material such as stainless steel, titanium, or other material. The sheath 72 is preferably made of a relatively stiff, biocompatible material such as stainless steel or an extruded or injection molded polymer.

FIGS. 4a and 4b illustrate an exemplary embodiment of a trigger 64 according to the present invention. A person skilled in the art readily understands that the trigger 64 may be designed and implemented in a number of ways. In this illustrative embodiment, the trigger 64 is pivotally connected to the handle 62 by a hinge 79. The trigger 64 may be, for example, a ratchet and pall arrangement with the release 78. Pressing a trigger release 78 causes the pall 80 to disengage from the ratchets 81. The trigger 64 is also connected to one end of an arm 82. The opposite end of the arm 82 is connected to a beak 68a. Pulling the trigger 64 causes the beak 68a to close in order to grasp a needle or suture.

Figure 5A:
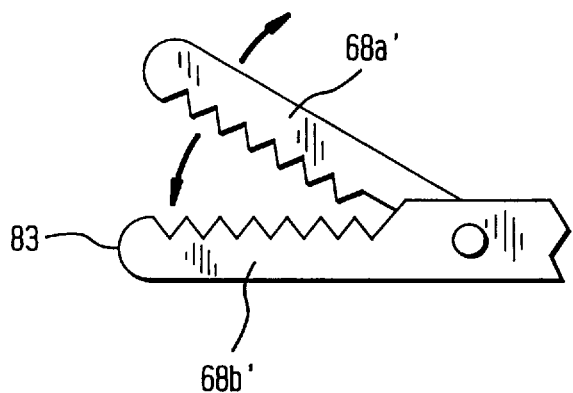
FIGS. 5a and 5b illustrate alternative embodiments of the needle holders according to the present invention.
Figure 5B:
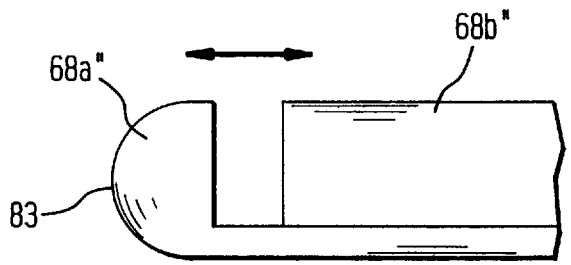

The needle holder 68a, 68b, may be either a grasper 68a', 68b', as shown in FIG. 5a, or a clamp, as shown by needle holder 68a", 68b", as shown in FIG. 5b. The dashed-line arrows indicate the needle holder movements. The grasper 68a', 68b' may be preferable because the surgeon is provided with more degrees of freedom to angle the needle held in the needle holder than with a clamp 68a", 68b". The very distal end of the needle holder 68a, 68b includes a surface 83 which may be used as a knot pusher. The clamp 68a", 68b" provides a larger surface 83 than the grasper 68a', 68b'.

As seen in FIGS. 4a and 4b, a lumen 84 extends through the hollow shaft 66 and the handle 62 to allow a suture 86 to pass through. At the distal end of the shaft 66 (seen in FIG. 4b), in the vicinity of the needle holder 68, is an aperture 88 which connects to the lumen 84, allowing the suture 86 to exit the distal end of the device 60. Similarly, a second aperture 89 is located near the proximal end of the device (seen in FIG. 4a) on the handle 62. The shaft also includes a device 90 for holding the suture taut while preparing the device for use. As illustrated in FIG. 4b, this device may be a flexible membrane made of, for example, an elastomeric membrane such as silicon, that will hold the suture taut. A person skilled in the art recognizes that any number of structures are equally suitable for holding the suture taut, such as a mechanical clamp, a clasp, reel, or other device.

The hollow shaft 66 may be axially rotatable. As shown in FIGS. 4a and 4b, this rotation may preferably be accomplished by connecting the handle 62 to knob 70. In this illustrative embodiment, the proximal end of the shaft 66 is fixedly connected to the knob 70. The knob 70 is axially, rotationally connected to the shaft 66. The sheath 72 is not connected to the shaft 66, and the shaft 66 is free to axially rotate with respect to the sheath 72.

The sheath 72 may be longitudinally positionable into a number of desired positions. Three positions are illustrated in FIG. 4b. The first position, which is optional to the operation of the present invention, is a fully extended position, shown in dashed lines. In this position, the sheath 72 covers the needle holder 68. The second position is an intermediate position, shown in solid lines in FIG. 4b. This position exposes the needle holder 68 and generally aligns the hook 74 with the needle holder 68. The third position is a fully retracted position, also shown in dashed lines in FIG. 4b. This position withdraws the hook 74 proximal to the needle holder 68. The purpose of these positions will be made apparent below.

The sheath may be retained in any of these three positions by the sheath positioner 76. As seen in FIG. 4a, the sheath positioner 76 may comprise a series of detents 92, at least one detent for each desired position. The sheath 72 may have one or more complementary-shaped indents 94 for mating with one of the detents 92. When the sheath is placed in the desired position, the indent 94 will mate with the appropriate detent 92, thus retaining the sheath in the desired position. Alternatively, the sheath positioner 76 may be self-centering to automatically return to a predetermined position, for example, the intermediate position, when not retained another position. This self-centering mechanism may include a spring 95 or other resilient device to return the sheath to a predetermined position, for example the intermediate position.

Figure 6:
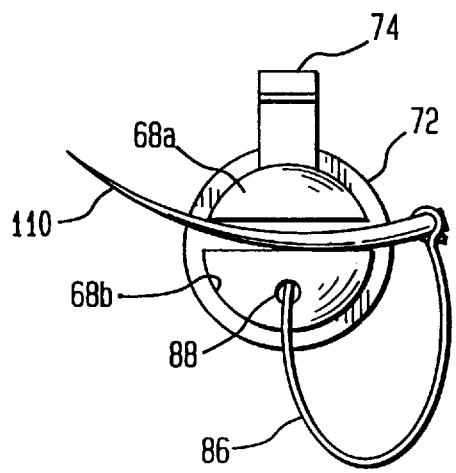
FIG. 6 is a front view of the device illustrated in FIGS. 4a and 4b.

FIG. 6 shows the front of a device 60 according to the present invention holding a needle 110 connected to a suture 86. The suture exits the device 60 through aperture 88 and is tied to an end of a needle 110. The needle is fly held in the needle holder 68.

Figure 1:
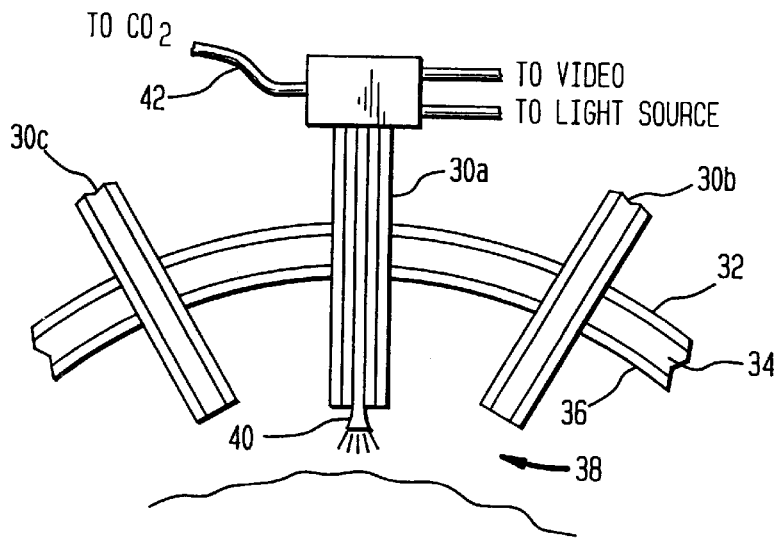
FIG. 1 is a cross-sectional view of a patient undergoing a laparoscopic surgical procedure.
Figure 2:
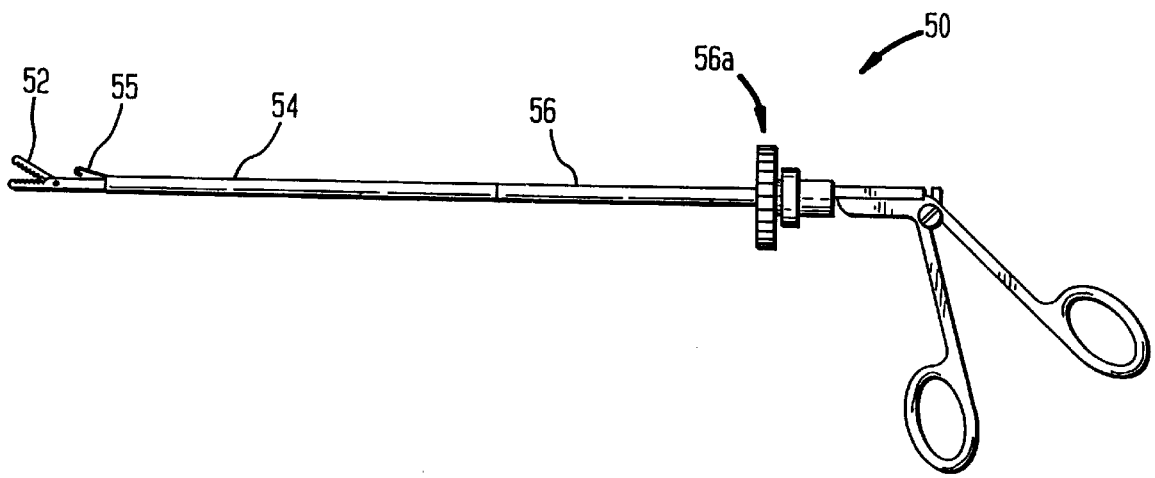
FIG. 2 is side elevational view of a prior art intracorporeal knotting device.
Figure 7:
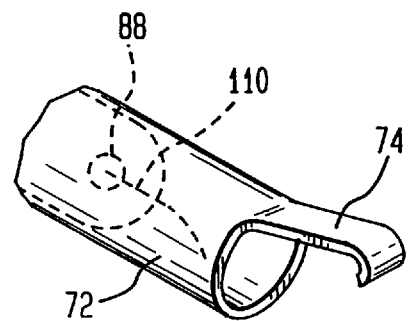
FIG. 7 is a perspective view of the device of FIG. 3 holding a needle and having a sheath covering the needle.

FIGS. 8–15 illustrate a preferred method of forming several "throws" of a knot, using the device illustrated in FIG. 3–7. Before the device 60 is inserted through a port to the surgical site, it should be prepared. To prepare the device for introduction to the surgical site, a proximal end of a suture 86 is placed into the hooked end of a guide wire. The guide wire is pulled through the distal end of the suture 86 through the shaft's lumen 84. The proximal end of the needle 110 is held within the lumen 84 and the sheath 72 may be placed in the fully extended position to cover the needle 110 and needle holder 68, as seen in FIG. 7, when inserted through a port (e.g., either 30b or 30c of FIG. 1) to the surgical site. The suture may be held taut by a suture holding device 90. The guide wire is removed from the suture 86.

Figure 8:
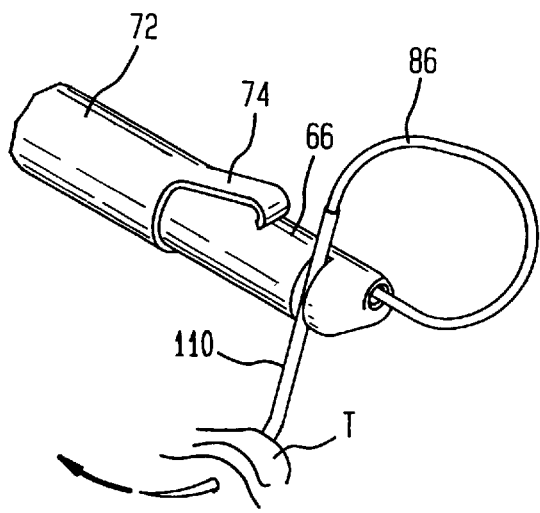
FIGS. 8–15 illustrate a method for tying a suture intracorporeally using one or more throws using the device of FIG. 3.

Once the device 60 is introduced to the surgical site, the sheath 72 is placed in the fully retracted position and a needle 110 is held in the needle holder 68 (a grasper is shown) and passed through tissue T to be sutured, as seen in FIG. 8. The needle 110 is disengaged from the needle holder 68 by releasing the tension by pulling the trigger 64.

Figure 9:
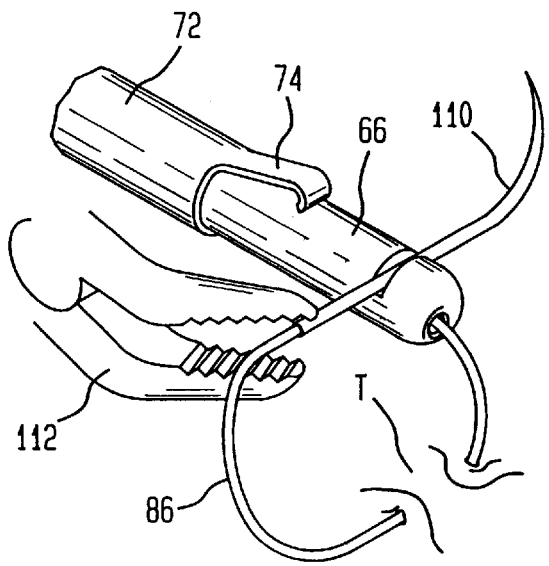

As seen in FIG. 9, a grasping instrument 112, introduced through another port, may be used to reposition the needle 110 back into the needle holder 68 and resecured by squeezing the trigger 64. An additional length of suture may be withdrawn by pulling proximally on the device 60. Additional suture may be needed, for example, to form suture loops or to chain multiple stitches. An alternative method for withdrawing additional suture length is by pulling on the needle 110 with the grasping instrument 112 before returning the needle to the needle holder 68.

Figure 10:
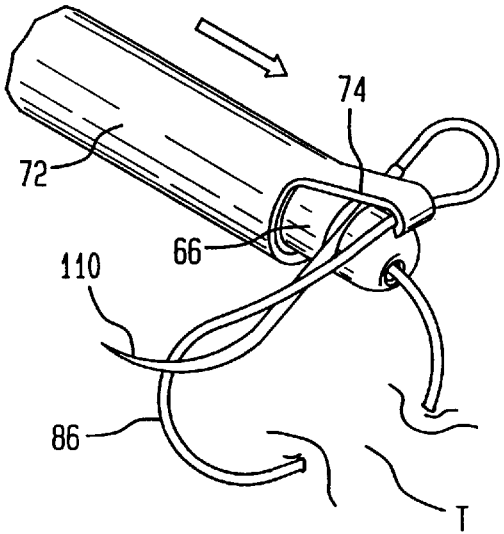
Figure 11:
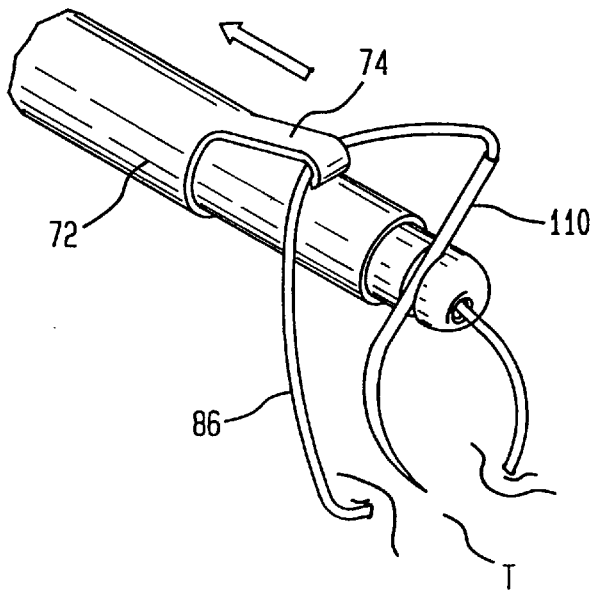

As seen in FIG. 10, the sheath 72 is moved forward to the intermediate position so that the hook 74 is in the vicinity of the needle holder 68 (an arrow indicates the direction of motion in FIGS. 10–15 and 17–21). The knob 70 is rotated so the shaft 66 rotates, causing the needle 110, held in the needle holder 68, to rotate. The rotation of the needle places the suture 86 in the hook's 74 path. The hook 74 snares the suture 86. Placing the sheath 72 into the withdrawn position, as seen in FIG. 11, causes the hook 74 to withdraw the suture 86 and creates a suture loop.

Figure 12:
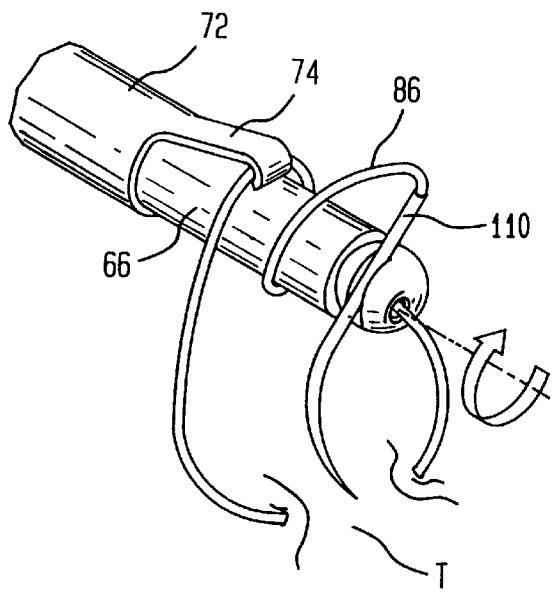
Figure 13:
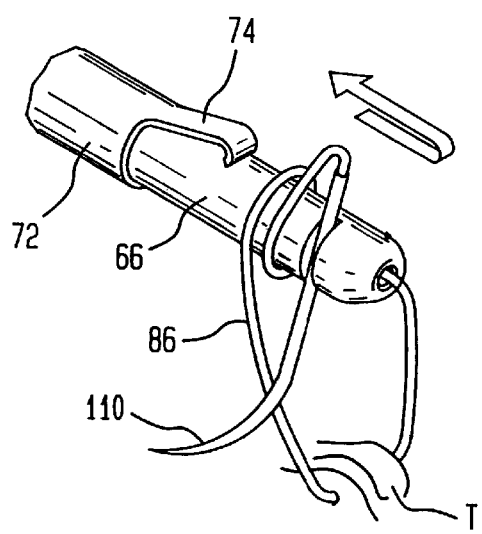

The knob 70 is now rotated so the suture 86 loops around the shaft 66, as seen in FIG. 12 (illustratively, the shaft is rotated clockwise). The shaft 66 may be rotated multiple times. Preferably, the shaft 66 is rotated twice to create two loops. Because the suture extends through the shaft 66, the loops are formed around the suture 86. Thus, there is no need to pull the needle 110 through the loops. Because the suture extends through the shaft there is no need to use a grasping instrument to hold the second leg of the suture 86. As seen in FIG. 13, the sheath 72 is moved forward to the intermediate position to release the suture 86 from the hook 74 and then placed in the withdrawn position to remove the hook from the vicinity of the needle holder 68.

Figure 14:
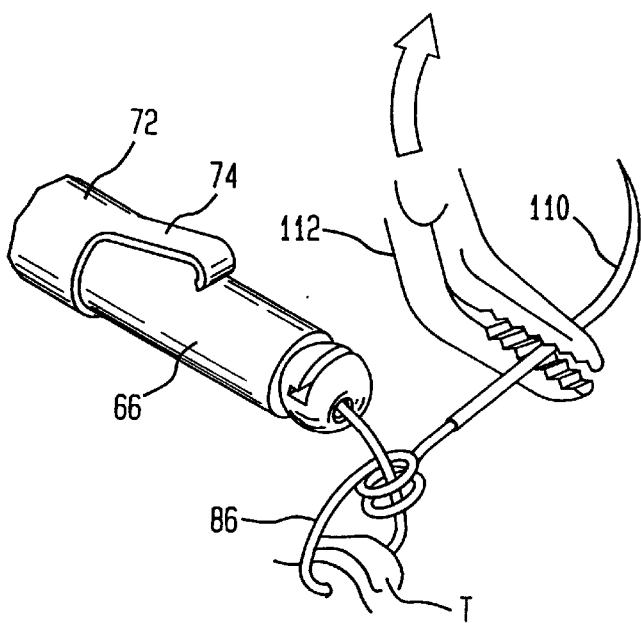

As seen in FIG. 14, the grasping instrument 112 may be used to remove the needle 110 from the needle holder 68. The throw may be cinched by pulling on the needle 110 with the grasping instrument 112 or, while pulling on the suture from the distal end of the device 60, the distal surface 83 of the device 60 may be used to push the knot into a closed stitch. Alternatively, pulling the proximal end of the suture 86 through the lumen 84 cinches the stitch. A third alternative is to pull proximally on the device 60 and with the grasping instrument 112 pull the suture 86 to cinch the stitch.

A locking throw may be formed by repeating these steps, but the shaft 66 is axially rotated in the opposite direction. For example, the throw illustrated in FIGS. 7–14 is formed by rotating the shaft clockwise. A locking throw for this knot is formed by rotating the shaft 66 counterclockwise.

Continuous sutures may be tied by providing enough suture and by placing the needle 110 back into the needle holder 68 and continue suturing. Additional single sutures may be performed by withdrawing and reloading the instrument.

Figure 15:
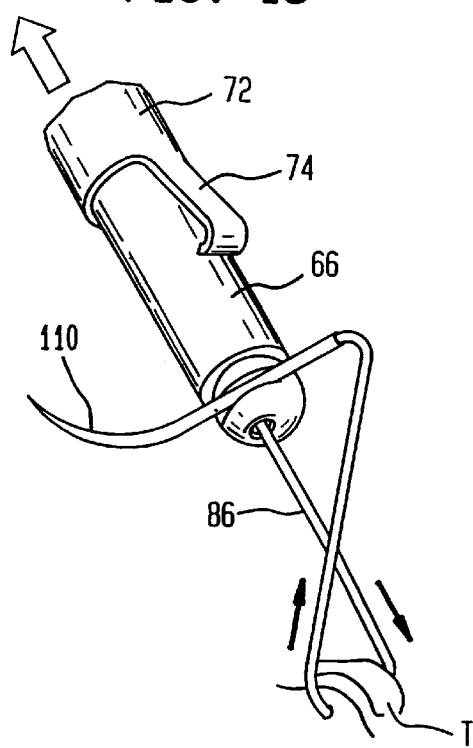

FIG. 15 illustrates an alternative method for releasing additional suture for another knot after the step illustrated in FIG. 9. The entire device 60 may be withdrawn proximally, or a forceps may be used to pull out additional suture.

FIGS. 16–21 illustrate an alternative embodiment and operation of the intracorporeal endoscopic suture tying aid of the present invention. This alternative device 260 has a pivotable hook 274 which is connected to a second arm 282 (shown in dashed lines in FIG. 16). Pulling the second arm 282 proximally causes the hook 274 to pivot upwards. The hook 274 may be a pivotal unit having a first portion that is a rod 275 and a second portion that is a hooked element 276. The distal end of the rod 275 is connected to a sheath 272 by a first pivot 278.

The sheath 272 is substantially as described above. The shaft 266 is also substantially as described above, except that it has a longitudinally slidable suture barrel 285 having a lumen 284 (the barrel and lumen are shown in dashed lines in FIGS. 16 and 18). Pushing on this barrel 285 distally causes it to extend out of an aperture 288 in a distal end of the shaft 266.

Figure 16:
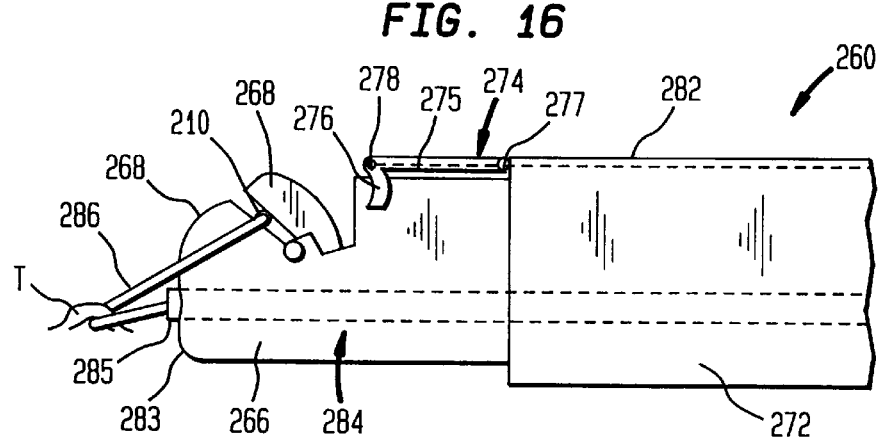
FIGS. 16–21 illustrate a preferred structure and operation of an alternative embodiment of an endoscopic intracorporeal tying aid according to the present invention; and a method for tying of a suture intracorporeally using this tying aid.
Figure 17:
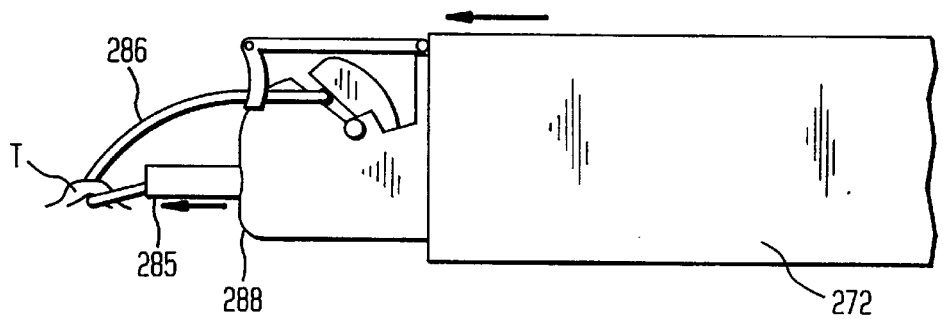

The device 260 is prepared and introduced as described above. A needle 210 is passed through tissue T to be sutured and repositioned into the needle holder 268 and resecured as described above, with the sheath 272 in the withdrawn position, as seen in FIG. 16. An additional length of suture 286 may be withdrawn from the device 260 by sliding the sheath 272 and barrel 285 forward so that the hook element 276 contacts the suture and the barrel 285 is located near the tissue to be sutured, as seen in FIG. 17. Extending the barrel 285 forward creates a larger controlled loop for the hook 274 to snare.

Figure 18:
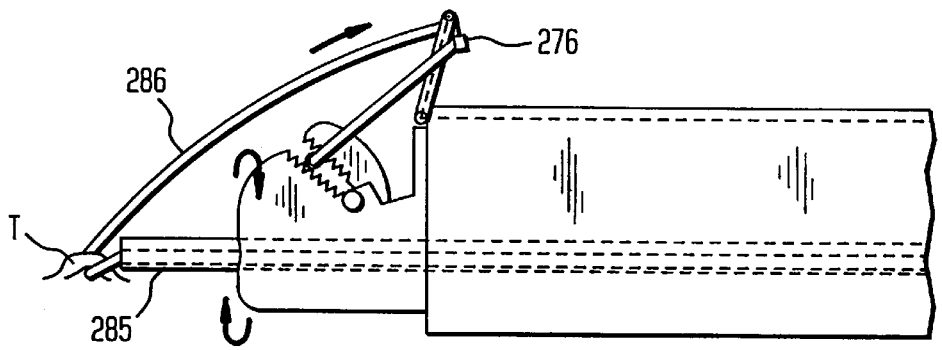

With the sheath 272 and barrel 285 in this position, the second arm 282 is moved proximally to pivot the hook 274 on pivot 288 so that the rod 275 and hook element 276 rotate backwards, as seen in FIG. 18. This pivoting movement pulls additional suture 286 from the barrel 285. The additional suture allows continuous suturing and a loop having a larger diameter than the loop created by the device illustrated in FIGS. 3–15. If a knot is desired (i.e., the beginning or end of a run of stitches), the shaft 266 is rotated, for example twice, looping the suture around the barrel 285, which is extended to the tissue being sutured.

Figure 19:
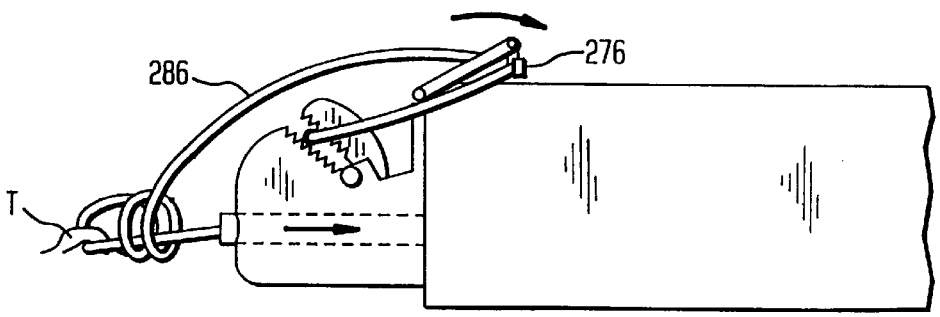
Figure 20:
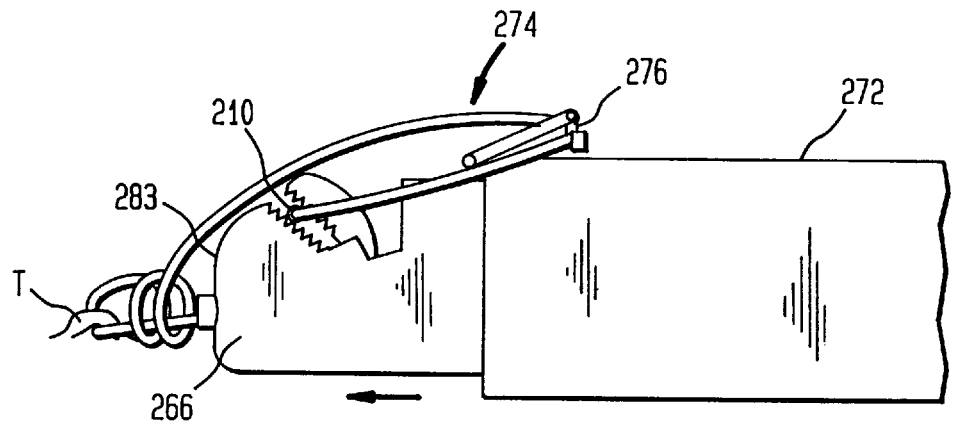
Figure 21:
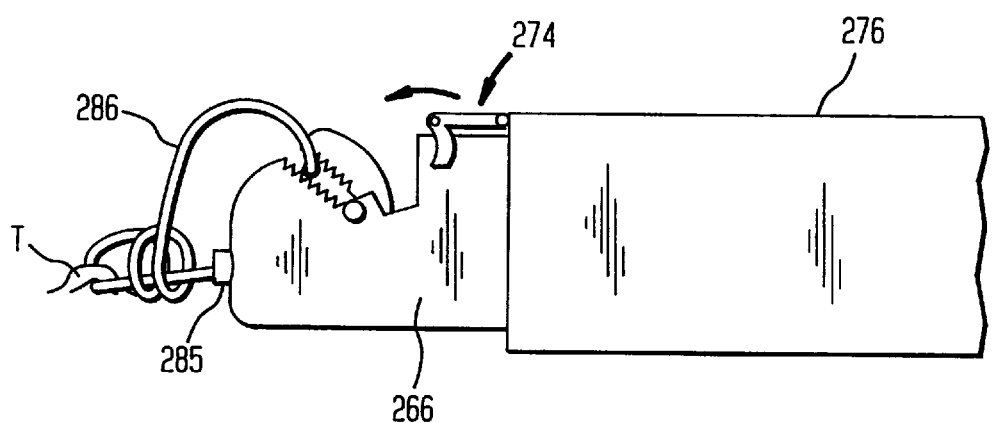

FIG. 19 shows the suture 286 having loops as the barrel 285 is withdrawn into the shaft 266. The hook 274 is further rotated proximally to secure the suture and its loop. This further rotation also increases the available suture length for continuous suturing. The shaft 266 is pushed distally towards the tissue to be sutured to operate as a knot pusher to cinch the throw closed with surface 283, as seen in FIG. 20. The pivotable arm 274 may then be rotated forward by pushing the second arm 282 distally so that the rod 274 and hook arm 276 rotate distally to release the suture 286, as seen in FIG. 21. Additional suture length is available for continuous suturing.

Figure 22:
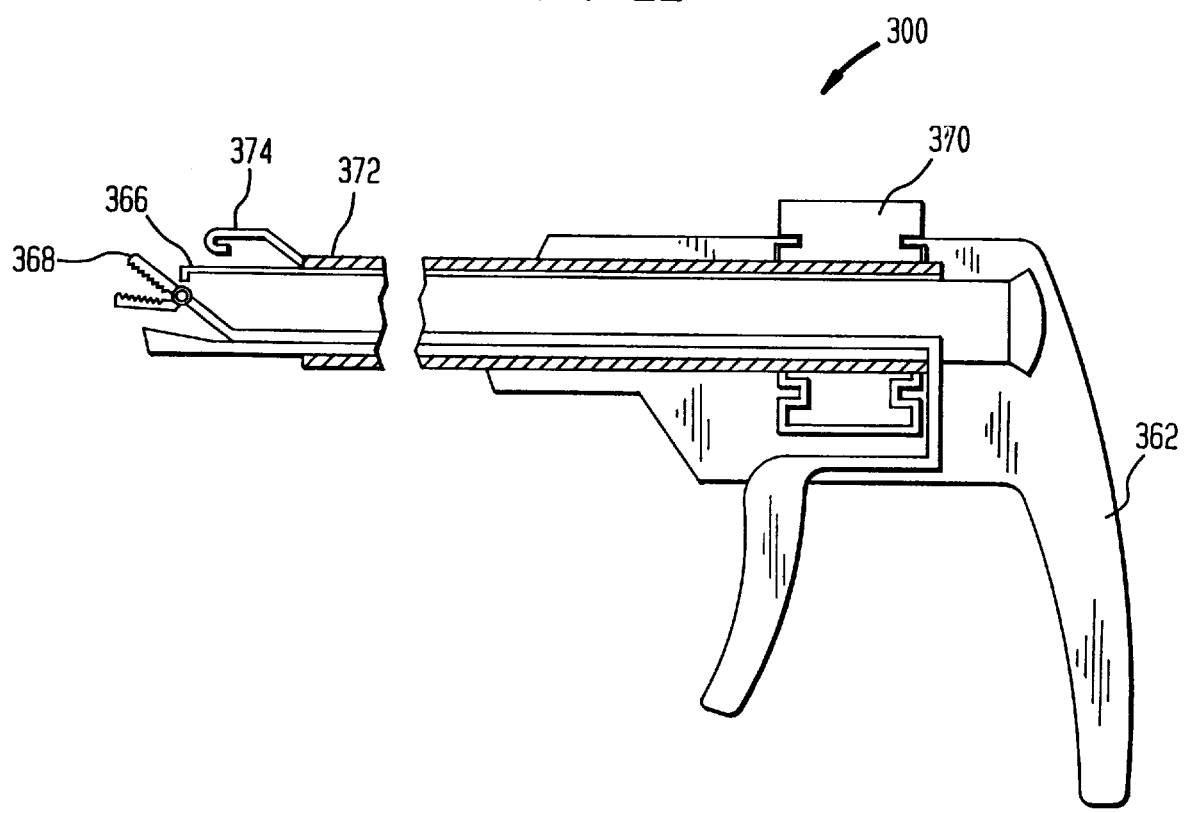
FIG. 22 is a cutaway view of a third embodiment of an endoscopic intracorporeal tying aid according to the present invention.

FIG. 22 illustrates another embodiment of an endoscopic suture tying aid according to the present invention. The endoscopic suture tying aid 300 has a hollow shaft 366 fixedly connected to a handle 362. A needle holder 368 is located at the distal end of the hollow shaft 366. A sheath 372 having a hook element 374 connected to a distal end of the sheath, is fixedly connected to a knob 370. Turning the knob 370 rotates the sheath 372 and therefore the hook 374 axially with respect to the needle holder 368. This device 300 is used in the same manner as illustrated in FIGS. 7–15, except that the hook 374 axially rotates with respect to the needle holder 368.

While the invention has been described by the reference to specific embodiments, this was for purposes of illustration only and should not be construed to limit the spirit or the scope of the invention. For example, although the invention has been illustrated with respect to laparoscopic surgery, a person skilled in the art readily appreciates that it may be applied to many areas of endoscopic surgery.

We claim:

1. An endoscopic suture tying aid, comprising:
   a. a shaft having:
      (i) an aperture near a distal end configured to allow a suture to extend therethrough; and
      (ii) a needle holder near the distal end, the needle holder being axially offset from the aperture;
   b. a sheath in longitudinally positionable contact with the shaft and configured to be positionable at least in a first position in the vicinity of the needle holder and a second position proximal to the needle holder;
   c. a hook connected to a distal end of the sheath and configured to engage a suture extending through the aperture and to pull the suture when moved from the first position to the second position; and
   d. the shaft and needle holder being axially rotatable in two directions with respect to the hook.

2. The endoscopic suture tying aid of claim 1, wherein the shaft includes a longitudinally slidable barrel having a lumen.

3. The endoscopic suture tying aid of claim 1, further comprising a lumen extending through the shaft and ending at the aperture, the lumen configured to receive the suture.

4. The endoscopic suture tying aid of claim 1, further comprising a handle, the handle having a trigger and a knob.

5. The endoscopic suture tying aid of claim 4, wherein the knob is connected to a proximal portion of the shaft and rotatably connected to the handle.

6. The endoscopic suture tying aid of claim 4, wherein the trigger is configured to selectively open and close the needle holder.

7. The endoscopic suture tying aid of claim 4, further comprising a sheath connected to the handle and longitudinally positionable with respect to the shaft, the hook being connected at a distal portion of the sheath.

8. The endoscopic suture tying aid of claim 7, wherein the hook is flexibly connected to the sheath.

9. The endoscopic suture tying aid of claim 7, further comprising a sheath positioner configured to retain the sheath so that the hook is selectively retained in at least one of the first and second positions.

10. The endoscopic suture tying aid of claim 9, wherein the sheath positioner comprises at least one receptacle in the sheath and a plurality of detents configured to engage the at least one receptacle.

11. The endoscopic suture tying aid of claim 9, further comprising sheath positioner means for automatically returning the sheath to the first position.

12. The endoscopic suture tying aid of claim 7, wherein the sheath is selectively positionable in a third position wherein the sheath substantially covers the needle holder.

13. The endoscopic suture tying aid of claim 1 where in the aperture is located distal to the needle holder.

14. The endoscopic suture tying aid of claim 1, wherein the needle holder is a grasper.

15. The endoscopic suture tying aid of claim 1, wherein the needle holder is a clamp.

16. The endoscopic suture tying aid of claim 15, wherein a distal part of the clamp is a knot pusher and the aperture is located on the knot pusher.

17. The endoscopic suture tying aid of claim 1, wherein the hook is configured to pivot with respect to the sheath.

18. The endoscopic suture tying aid of claim 17, wherein the hook comprises a hook configured to revolve around the shaft.

* * * * *